United States Patent [19]
Heimur

[11] 3,936,641
[45] Feb. 3, 1976

[54] HEAD IMMOBILIZING DEVICE FOR PANORAMIC X-RAY APPARATUS

[75] Inventor: Karl Heimur, Newdorp, N.Y.

[73] Assignee: Pennwalt Corporation, Philadelphia, Pa.

[22] Filed: Oct. 21, 1974

[21] Appl. No.: 516,344

[52] U.S. Cl. ............... 250/439; 250/45 G; 269/328
[51] Int. Cl.² ........................................ G03B 41/16
[58] Field of Search ................. 250/451, 45 G, 439; 269/328

[56] References Cited
UNITED STATES PATENTS

| | | | |
|---|---|---|---|
| 2,032,833 | 3/1936 | Broadbent | 250/456 |
| 3,099,441 | 7/1963 | Ries | 269/328 |

*Primary Examiner*—Craig E. Church
*Attorney, Agent, or Firm*—Edward A. Sager

[57] ABSTRACT

An improved head immobilizing device for use with panoramic x-ray machines is provided. The improvements reside principally in a mechanism for adjusting the level of the chin rest in vertical direction and for securing the same by means of a screw device employing two threads of different pitch. The arms which engage the sides of the patient's head are positioned by movement of horizontal, spaced rods driven by a simplified drive mechanism employing either an H-shaped plate contacting rollers on the rods or a drive member connected to the rods by means of links.

10 Claims, 7 Drawing Figures

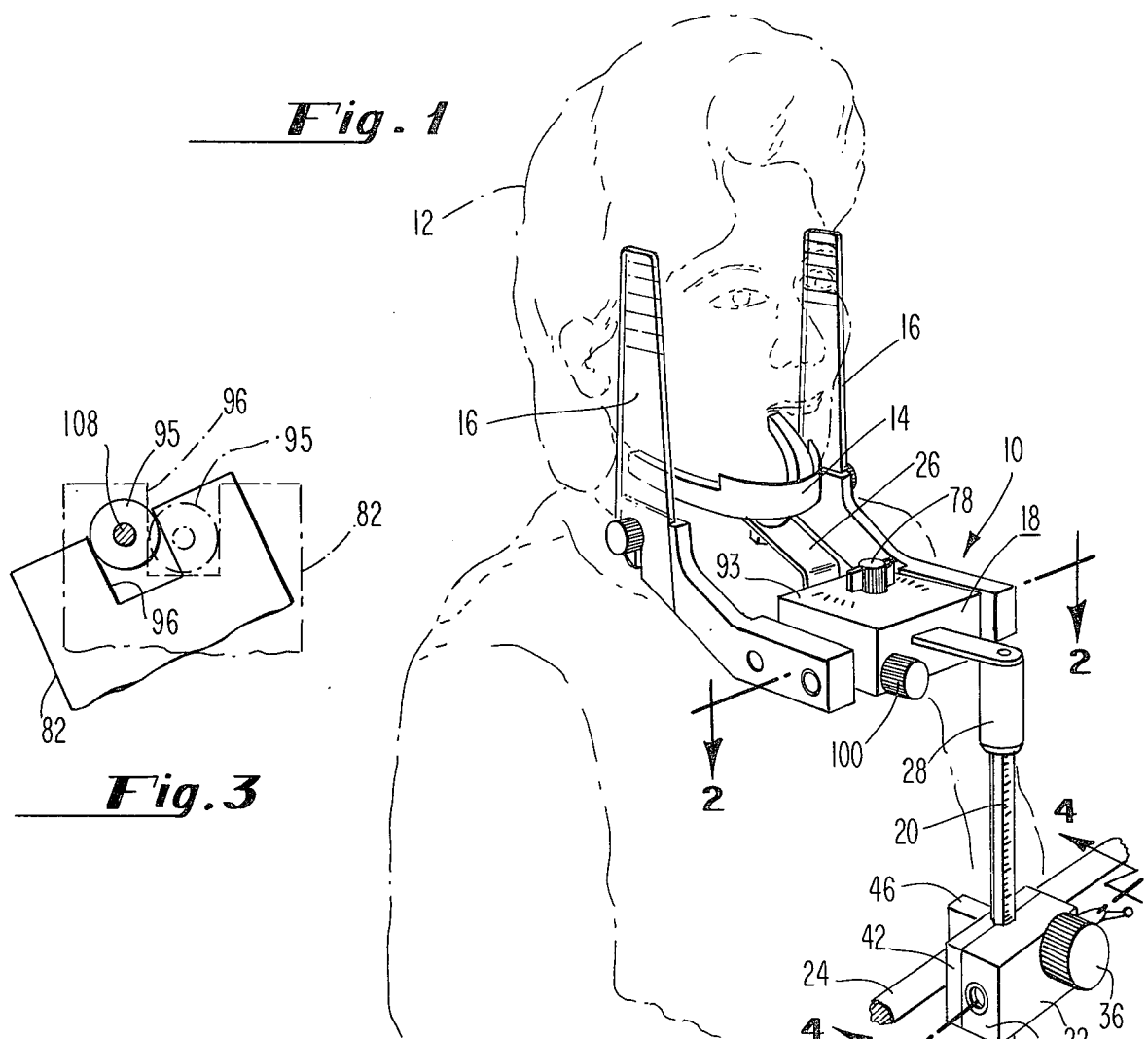
Fig. 1
Fig. 3
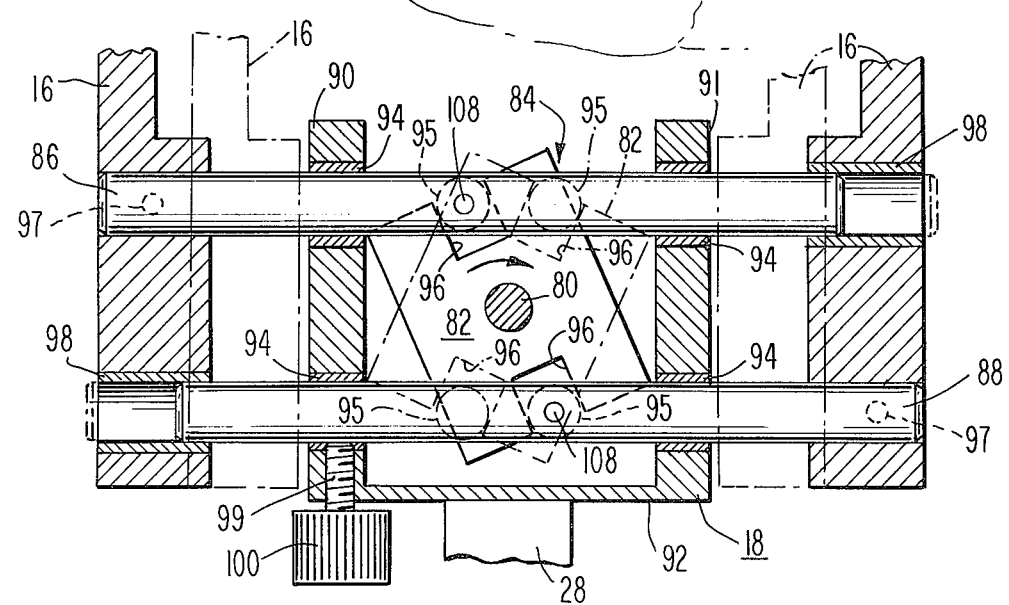
Fig. 2

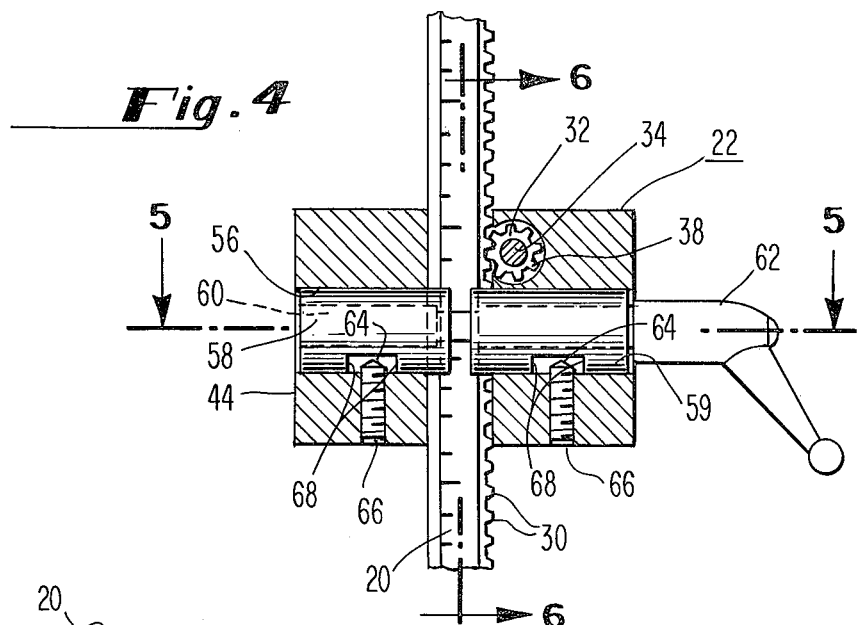
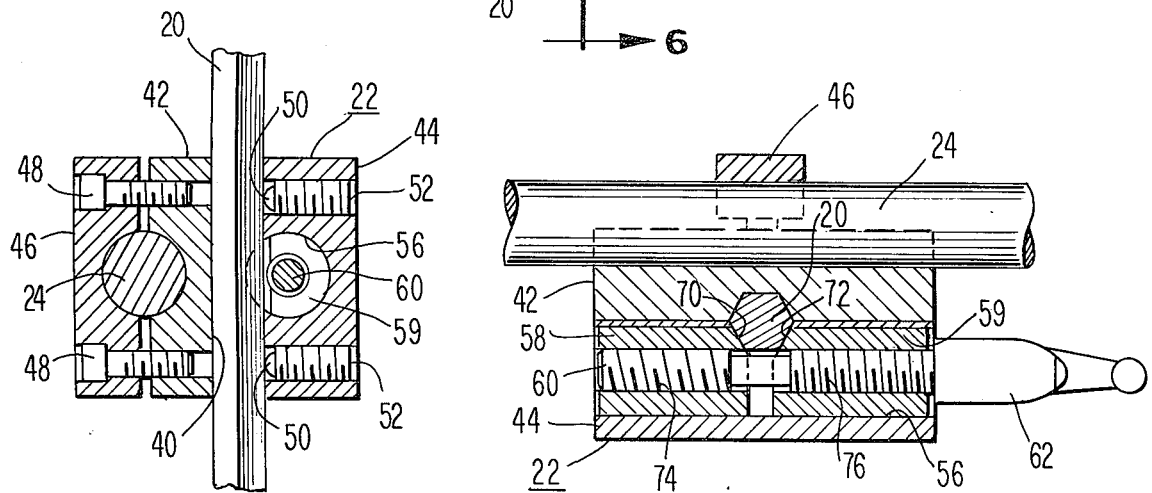
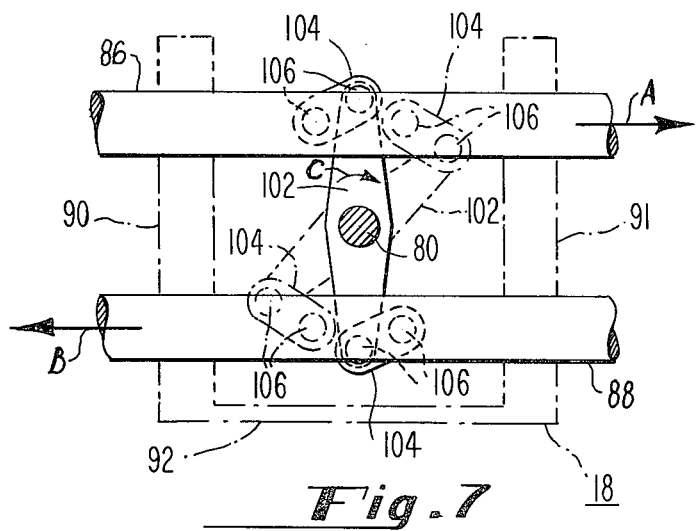

3,936,641

HEAD IMMOBILIZING DEVICE FOR PANORAMIC X-RAY APPARATUS

BACKGROUND OF THE INVENTION

This invention relates to devices for immobilizing and sizing the human head when making panoramic radiographs of a portion of such head, for example, the full dental arch. More particularly, it is an improvement upon the device disclosed in U.S. Pat. No. 3,521,057 of A. F. Morlan, granted July 21, 1970, to which reference is hereby made, mainly regarding the purposes, application, and objectives of devices of this kind and their operative association with the chair and panoramic x-ray apparatus.

SUMMARY OF THE INVENTION

An improved head immobilizing device for use with panoramic x-ray machines is provided. The improvements reside principally in a mechanism for adjusting the level of the chin rest in vertical direction and for securing the same by means of a screw device employing two threads of different pitch. The arms which engage the sides of the patient's head are positioned by movement of horizontal, spaced rods driven by a simplified drive mechanism employing either an H-shaped plate contacting rollers on the rods or a drive member connected to the rods by means of links.

BRIEF DESCRIPTION OF THE DRAWINGS

In the drawings:

FIG. 1 is a perspective view of the head immobilizing device made according to the present invention and shown in relation to a seated patient.

FIG. 2 is a horizontal, sectional view of the device taken along line 2—2 of FIG. 1 and represented on an enlarged scale.

FIG. 3 is an enlarged view of a fragment of FIG. 2 showing the drive mechanism in further detail.

FIG. 4 is a vertical, sectional view taken along line 4—4 of FIG. 1, and enlarged to show the elevating mechanism in detail.

FIG. 5 is a horizontal, sectional view through the elevating mechanism of FIG. 4, taken along line 5—5.

FIG. 6 is a vertical, sectional view of the elevating mechanism of FIG. 4 taken along line 6—6 of FIG. 4.

FIG. 7 is a view, partly in elevation, partly in vertical section, and partly in phantom, similar to FIG. 2, but showing a modification of the drive mechanism for the support rods.

PREFERRED EMBODIMENT OF THE INVENTION

Shown in FIG. 1 is the device 10 of the present invention applied to a person 12, having her chin supported on a chin rest 14 and her head held between a spaced pair of upright arms 16. The chin rest 14 and arms 16 are carried by a housing 18, in a manner to be described. The housing 18 is supported on an upright bar 20 which is movably held by a gear box 22. The gear box 22 is secured to a horizontal cross-bar 24, the latter being supported on the arms of a patient chair (not shown) in a manner well known in the art.

The chin rest 14 is rigidly connected to the housing 18 by a bracket 26, and the housing 18 is rigidly connected to the bar 20 by an elbow 28, whereby the chin rest 14 and housing 18 are unitarily movable with the bar 20 when the bar 20 is moved in vertical direction. The bar 20 is preferably of generally hexagonal cross-section, as shown in FIG. 5; and it is provided with gear teeth 30 along one vertical side thereof, as shown in FIG. 4, to provide the gear rack portion of a rack and pinion 32 assembly. The shaft 34 of the pinion 32 extends through the front wall of the gear box 22; and a knob 36 is rigidly secured to the free end of the pinion shaft 34 to facilitate manual rotation of the pinion 32. Since the teeth 38 of the pinion 32 and the teeth 30 of the bar 20 are arranged to cooperatively engage, manual rotation of the knob 36 will effect vertical movement of the bar 20 relative to the gear box 22. The front surface of the bar 20 is provided with indicia, uniformly graduated to permit recording of the elevation of the chin rest 14, so that a radiograph may be repeated for a particular patient with the patient's chin and head positioned as previously.

Referring now to FIGS. 5 and 6, the bar 20 is vertically slidable in a vertical passageway 40 through the gear box 22, such passageway being formed by the mutually facing, vertical surfaces of the two parallel plates 42, 44 which comprise the gear box 22. The front plate 44 is more distant from the patient; and the rear plate 42 is closest to the patient. The cross-bar 24 is secured to the gear box 22 by means of a clamping member 46 and two screws 48 for connecting the clamping member to the plate 42. The bar 20 is contacted by the rounded tips 50 of respective screws 52, employed to position and to frictionally engage the front surface of the bar 20, such screws 52 being fitted to cooperating threads in the front plate 44 of the gear box 22.

In order to lock the bar 22 in selected vertical position, a locking device 54 is provided. Most of the parts of the locking device 54 are movable within a horizontal passageway 56 in the front plate 44, such passageway 56 being oriented to intersect the vertical passageway 40 intermediate the ends of both passageways, although the axes of the two passageways are spaced apart a small distance.

The locking device 54 further includes a pair of movable vise jaws 58, 59 of tubular construction, threaded to, and carried on, an internal screw 60 which may be rotated by a handle 62. The jaws 58, 59 are movable in horizontal direction within the passageway for a short distance, limited by the tips 64 of screws 66 and the adjacent abutment surfaces 68 of respective grooves formed in the lower central portion of each of the jaws 58, 59.

The vise jaws 58, 59 each have a beveled end portion respectively designated 70 and 72, and adapted to engage the bar 20 between them. The bevel angle at each end portion 70, 72 is 30° from a plane normal to the axis of the screw 60, in order to maintain parallelism with the contact surface of the bar 20.

As best seen in FIG. 5, the screw 60 has a first threaded end portion 74 cooperatively threaded, preferably with a ⅜-16 thread, to vise jaw 58, and a second threaded end portion 76 cooperatively threaded, preferably with a ⅜-24 thread, to vise jaw 59. Because of the difference in the pitch of the threads of the respective end portions 74 and 76, rotation of the screw 60 by the handle 62 effects relative motion of the two vise jaws 58 and 59. When the screw 60 is rotated in one direction about its rotational axis, the vise jaws 58 and 59 move apart and loosen their grip on the bar 20; and, when the screw 60 is rotated in opposite direction, the vise jaws move toward one another and tighten their grip on the bar 20. Both threads are coiled in the same direction, that is, are right hand threads but left hand threads may also be used.

Of course, the invention is not limited to the thread sizes and the thread pitches specified above. It is necessary that there be a difference in pitch to effectuate the operation of the present device. With the illustrated arrangement, a 50:1 mechanical advantage is obtained. The bar 20 is securely held, with little chance of loosening until it is done deliberately by turning the handle 62.

Movement of the arms 16 toward and away from one another is accomplished by turning the knob 78 on the top of the housing 18, thereby turning shaft 80 on the upper end of which knob 78 is mounted, and simultaneously rotating the drive plate 82 mounted on the bottom end of shaft 80. By drive means 84 to be described hereinafter, rotation of the drive plate 82 effects movement in opposite directions of a pair of horizontally spaced, support rods 86, 88 for the respective arms 16.

The housing 18 is comprised of a pair of horizontally disposed side walls 90, 91 and a front wall 92, all joined together in a "U" shape and further provided with a top cover plate 93. The side walls 90, 91 are provided with cylindrical bushings 94, arranged in aligned pairs to support each of the support rods 86, 88 for sliding movement therein. Each of the support rods 86, 88 has a roller 95 mounted on the underside thereof, midway between its ends; and each roller 95 is snugly received in one of the rectangular notches 96 formed in the drive plate 82 on opposite sides of the axis of the shaft 80.

In FIG. 2, solid lines are employed to show the position of ports when the arms 16 are separated the maximum distance, with the rods 86, 88 fully extended from the housing 18; and broken lines are employed to show the position of ports when arms 16 are separated the minimum distance, with the rods 86, 88 retracted about as far as possible. In both extreme positions shown, the rollers 95 are in contact with the edge surfaces defining the respective notches 96, but with each roller partly out of its associated notch, whereas each roller is positioned well down in its associated notch in the intermediate position of the plate 82 shown in broken lines in FIG. 3. It will be appreciated that such movement of the rollers 95 relative to the notches 96 results from the translation of angular or rotational motion of the drive plate 82 to linear motion of the rods 86, 88, with the drive plate 82 maintaining driving and rolling contact with the rollers 95 in all angular positions of the drive plate.

A rigid driving connection between each of the rods 86, 88 and its associated arm 16 is maintained by means of a screw 97 which passes upwardly through the underside of the generally horizontal portion of the L-shaped arm 16 and well into the end portion of the associated rod, there being a secure, threaded connection of the screw 97 therewith. Each arm 16 is further supported, as against rotation in a vertical plane about the rod to which it is connected, by means of the sliding support afforded by the free end of the other rod being received in a bushing 98. Each of the two bushings 98 is also rigidly mounted in the horizontal portion of its respective arm 16, all of which is seen in FIG. 2. Further provided is a locking screw 99, threaded to the front wall 92 of the housing 18, which may be manually turned by a knob 100 into locking engagement with the rod 88 in order to hold the arms 16 in position, after positional adjustment of the arms has been achieved by rotation of the knob 78. The arrangement is such that the free end of each rod is slidable within its bushing 98 during movement of the knob 78, and that in any position of the knob 78 at least a portion of the free end of a rod will be within its associated bushing 98.

MODIFICATION

In FIG. 7 is shown a modified embodiment of the invention, the modification being directed to means, for driving the rods 86 and 88 in opposite horizontal directions, which perform the same functions as the drive plate 82 and the rollers 95. Where identical parts are employed in the embodiments of FIGS. 2 and 7, the same reference numerals are used.

In the embodiment of FIG. 7, the shaft 80 has rigidly connected to the lower end thereof a drive member 102 which extends, in opposite horizontal directions from the axis of the shaft 80, a radial distance beyond the longitudinal axes of the respective rods 86, 88. To each end of drive member 102 there is pivotally connected a link 104 which extends to about the longitudinal axis of its associated rod, where it is again pivotally connected. The four pivotal connections just described are made by pivot pins 106. Rotation of the shaft 80 in clockwise direction, as shown in FIG. 7, turns the drive member 102 from the solid line position to the broken line position illustrated in this view, carrying therewith the links 104 and the rods 86, 88, thereby moving the rods horizontally in opposite direction. Reverse rotation of the shaft 80 effects reverse movement of the associated parts, more particularly movement of the rods 86, 88 back toward starting position.

OPERATION

The head immobilizing device 10 is placed into use by first securing the horizontal crossbar 24 to the patient chair (not shown) in front of the seated patient 12. By rotating the handle 62, the grip of the locking device 54 is loosened on the upright bar 20. Then, the chin rest 14 is adjusted to the elevation of the patient's chin by manipulation of the knob 36; and, with the patient's chin resting on the chin rest 14, the upright bar 20 is secured by tightening the locking device 54 by rotation of the handle 62. An advantage of the present invention, as compared with prior art constructions, is that the chin rest 14 and its supporting structures will extent horizontally at right angles to the crossbar 24 because of the peculiar hexagonal cross-section of the bar 20 and the mating parts of the locking device 54 disposed within the gearbox 22, as best seen in FIG. 5. In addition, as pointed out previously, the different pitches of the threads on the end portions 74 and 76 of the screw 60 provided a convenient, quick, and dependable means for securing the locking device.

The upright arms 16 are widely spaced apart in starting position, when the patient is seated. After the chin rest 14 has been set as noted above, the operator turns the knob 78 in order to move the arms 16 toward one another until they engage the sides of the patient's head, at which time the knob 100 is turned to secure the arm support rods 86 and 88 in such position. It will be seen in FIG. 1 that the knob 78 is equipped with a pointer for cooperation with the indicia on the top cover plate 93 of the housing 18. The particular designation corresponding with the position of the pointer indicates the patient's head size, which information is needed for making the panoramic radiograph. By recording this information and the elevation of the chin rest, as may be read from the indicia on the bar 20, another radiograph may be taken at a later date for comparsion, with assurance that the patient's head position is substantially the same.

The device of the present invention is believed to have a chin rest positioning and securing means which is more convenient and more reliable than any previously known to the art. In addition, the mechanism for moving the arm support rods 86, 88 is believed to be less expensive to manfacture, less complex and at least as dependable as prior art devices of this kind. In particular, the device of the present invention does not require the manufacture of expensive gear racks for operation with a pinion, but instead employs inexpensive rods and inexpensive drive mechanisms in order to move the arms 16 in horizontal direction.

Although not essential to the present invention, mention is made here of the construction of the arms 16 with reference to FIG. 1. The arms 16 are generally L-shaped, including an upright portion which may be made of clear plastic material with horizontal graduations at the end thereof. The upright portion is secured to a rigid, horizontal portion by providing a vertical slot in the lower end of the upright portion which will fit over a screw secured to the horizontal portion when the knob at the free end of the screw is rotated.

The device of the present invention may be made entirely of steel or other metal material, although for such items as the chin rest 14 and the knobs 78, 100, 36 and the aforementioned parts of the arms 16, plastic material is recommended.

The links 104 are pivotally mounted to the rods 86 and 88 so that the rods will move in the directions shown by arrows A and B when the drive member is rotated in the direction shown by the arrow C, according to FIG. 7. In the embodiment of FIG. 2, the rollers 95 are pivotally connected to the rods by pivot pins 108.

What is claimed is:

1. In a human head immobilizing device for panoramic x-ray apparatus, the combination of
   a. a pair of horizontally spaced, upright arms movable in horizontal directions, adapted to contact the sides of a patient's head,
   b. a chin rest disposed between the lower portions of said arms, adapted to receive a patient's chin thereon,
   c. a housing rigidly supporting said chin rest and also movably supporting said arms,
   d. an elongated, upright bar carrying said housing and depending downwardly therefrom, and
   e. improved supporting means engaging a lower portion of said bar and providing vertically adjustable support therefor, said supporting means including
   f. a gear box,
   g. a toothed rack extending longitudinally on one side of said upright bar and being slidable through said box in generally vertical direction with said upright bar,
   h. a pinion rotatable within said gear box engaging said toothed rack to move it in opposite vertical directions,
   i. knob means outside said gear box and connected to said pinion for manually rotating said pinion, whereby the elevation of said chin rest and said arms is adjustable, and
   j. a vise operatively associated with said gear box for securing said upright bar in selected vertical positions, comprising first and second movable jaws and a screw cooperatively threaded to said jaws.

2. The device of claim 1 wherein said screw has first and second portions threaded independently of one another to said first and second movable jaws, respectively, and wherein the threads of said first and second portions of said screw are coiled in the same direction but are of substantially different pitch.

3. The device of claim 2 wherein said screw extends horizontally in said gear box and projects from one side thereof, being further provided with a handle for rotating said screw to tighten or loosen the grip of said vise on said upright bar.

4. The device of claim 1 wherein said upright bar is of polygonal cross-section, and said gear box and said vise jaws define a vertical passageway of corresponding cross-sectional shape for said upright bar in said gear box, whereby angular movement of said vertical bar about its longitudinal axis is resisted by said passageway.

5. The device of claim 1 wherein said housing is provided with a pair of closely spaced, generally parallel rods, each having one end portion connected to the respective arms in rigid driving relationship on opposite sides of said housing, said rods being supported by said housing for horizontal sliding movement relative thereto, and drive means carried by said housing and engageable with said rods for driving said rods in opposite horizontal directions.

6. The device of claim 5 further including a cam follower pivotally mounted on each of said rods.

7. The device of claim 6 wherein said drive means comprises a generally H-shaped plate provided by a plate having a pair of generally rectangular notches formed therein, which notches receive the respective cam followers in driving relationship therewith, and said plate being mounted in said housing for rotation about a generally vertical axis passing between said notches, and means connected to said plate for manually rotating said plate.

8. The device of claim 6 wherein said drive means comprises a horizontally disposed member mounted within said housing for rotation about a generally vertical axis, and means pivotally linking said cam followers to said member on opposite sides of the rotational axis of said member to provide a driving relationship between said member and said rods, and means connected to said member for manually rotating said member.

9. The device of claim 6 further including a locking screw cooperatively threaded to said housing, for movement inwardly of said housing into engagement with at least one of said rods for locking the upright arms in selected position, and for movement outwardly of said housing for disengagement with said one of said rods for unlocking the upright arms.

10. The device of claim 6 further including indicia on said housing corresponding to the angular position of said drive means to indicate the horizontal distance between said upright arms, and indicia on said upright bar corresponding at said gear box to the elevation of said chin rest.

\* \* \* \* \*